United States Patent [19]

Horsler et al.

[11] 3,959,160

[45] May 25, 1976

[54] AEROSOL SHAVING FOAM COMPOSITIONS

[75] Inventors: Christopher Horsler, Amersham; John Piercy, Leek, both of England

[73] Assignee: Wilkinson Sword Limited, Great Britain

[22] Filed: May 13, 1974

[21] Appl. No.: 469,052

[52] U.S. Cl. ................................. 252/90; 252/307; 252/DIG. 13; 424/73
[51] Int. Cl.² ........................................ C11D 17/00
[58] Field of Search ...................... 252/90, DIG. 13; 424/73

[56] References Cited
UNITED STATES PATENTS

| | | | |
|---|---|---|---|
| 2,344,671 | 3/1944 | Bertsch | 252/73 |
| 2,655,480 | 10/1953 | Spitzer et al. | 252/90 |
| 2,908,650 | 10/1959 | Fine | 252/90 |
| 2,942,008 | 6/1960 | Lubowe | 424/73 |
| 2,987,446 | 6/1961 | Riethmuller | 424/73 |
| 3,178,352 | 4/1965 | Erickson | 252/DIG. 13 |
| 3,190,802 | 6/1965 | Zeile et al. | 424/73 |
| 3,821,116 | 6/1974 | White | 424/73 |
| 3,870,660 | 3/1975 | Paviak | 252/DIG. 13 |

*Primary Examiner*—William E. Schulz
*Attorney, Agent, or Firm*—Brooks Haidt Haffner & Delahunty

[57] ABSTRACT

According to the invention improved aerosol shaving foams are obtained having scum-free and scum-dispersant properties coupled with good storage stability of the aerosol emulsion in the aerosol container, these foams being derived from, as the foamable base, an aqueous concentrate containing a particular combination of surfactant materials and a long chain fatty alcohol.

7 Claims, No Drawings

AEROSOL SHAVING FOAM COMPOSITIONS

FIELD OF INVENTION

This invention relates to pressurised shaving foam dispensers of the so-called aerosol type, and more particularly to the formulation of the foamable compositions used therein.

BACKGROUND OF INVENTION

In pressurised shaving foam dispensers of the above-mentioned type, a foamable concentrate, generally an aqueous soap solution, is contained in a dispenser equipped with a dispensing head and valve, and pressurised with a normally gaseous propellant, e.g. a low molecular weight hydrocarbon or hydrocarbon mixture or a halohydrocarbon or halohydrocarbon mixture. In the container the liquefied propellant forms an emulsion in the foamable concentrate, the emulsion being referred to as an aerosol emulsion. Upon discharge of the emulsion through the dispensing head the volatilization of the dispersed liquid droplets of propellant causes the dispensed concentrate to foam. Depending upon the precise formulation of the concentrate, the dispensed product may range from a dense creamy foam to a light lather.

For the avoidance of doubt, the term 'emulsion' will be used throughout this specification and claims to refer to the whole liquid contents of the dispenser, i.e. the foamable concentrate plus liquid phase propellant, and the term 'concentrate' will be used to refer to the liquid contents of the dispenser, other than the propellant, 'liquid' in this context embracing solutions, emulsions and suspensions. In other words, the concentrate itself may be an emulsion or suspension and not necessarily a solution of the foam producing ingredients in a suitable liquid medium, which in the case of the present invention will be water.

Various disclosures have been made of compositions suitable for use in such dispensers, amongst which may be mentioned U.K. Pat. Specification No. 838,913 and U.S. Pat. No. 2,655,480. In accordance with the proposals of U.K. Pat. Specification No. 838,913 aqueous soap solutions are used in which the quantity of alkali metal, ammonium or alkylamine soaps, or soaps of primary or secondary alkanolamines, is kept below 4%, based on the weight of the concentrate, and in which the amount of triethanolamine soap is kept in minor proportion relative to the total soap content. In accordance with U.S. Pat. No. 2,655,480 aqueous soap solutions are also used, the actual concentration varying with the particular soap used. Thus, when triethanolamine stearate is used the concentration may be from 2–30% by weight of the solution and when potassium stearate is used the recommended amount is from 5 to 20%. A generally recommended range for all soaps is 5 to 18%.

Yet other aqueous soap solutions are disclosed in U.S. Pat. No. 2,908,650, these being aqueous solutions of alkali metal soaps and soaps of nitrogen bases in specified proportions.

In such prior compositions a variety of additives have been proposed or used to modify or control the properties of the foam or emulsion. For example, U.S. Pat. No. 2,655,480 discloses that water-soluble non-ionic or anionic wetting agents may be added in amounts up to 5 or 6%, based on the weight of the concentrate, to facilitate rinsing of the lather from the face and avoiding oily deposits on the skin. Particular anionic and non-ionic wetting agents mentioned are sodium lauryl sulphate, sodium dodecyl benzene sulphonate, and watersoluble polyoxyethylene ethers of alkyl-substituted phenols. In addition, glycerine may also be added to stabilize the lather. U.K. Pat. Specification No. 838,913 discloses the addition of small amounts (1–3%) of water-soluble emulsifiers, e.g. fatty acid esters of polyhydricpolyoxyethylenated alcohols and fatty acid alkanolamides. U.K. Pat. No. 838,913 also discloses the addition of water-insoluble fatty acids, fatty alcohols and their ethylene oxide derivatives, to give the lather a creamy character and effect a slight fatting of the skin. In addition, U.K. Pat. No. 838,913 further teaches the addition of relatively high amounts (up to 15%) of water-insoluble free fatty acid to effect stabilization of the lather.

Reference may also be made to the studies reported in J.Soc. Cosmetic Chemists, 17, (1966), pages 801–830 on the effects of the addition of long chain fatty alcohols to aqueous aerosol emulsions based on anionic surfactants, in particular, on certain triethanolamine soaps and on sodium lauryl sulphate. In general, the addition of long chain alcohols to these emulsions showed an increase in viscosity and emulsion stability, judged on the time required for phase separation after hand shaking. Increases were also noted in foam stability and foam stiffness.

Although soap-based aerosol shaving foams have attained a certain degree of popularity, the formulations currently used have certain disadvantages, the foremost of which is the tendency, when used, to form a scum either in the form of hardwater deposits, particularly, of course, when used in hard water areas, or in the form of free fatty acid. This scum, in turn, forms unsightly deposits around the wash basin and, more particularly, on the razor and because of the difficulty of removing these deposits, which are often not removed by simple rinsing, the razor rapidly becomes encrusted.

Soapless aerosol foams based on synthetic surfactants and containing a synthetic surfactant in combination with a long chain fatty acid or alcohol have been described. For example, in Soap and Chemical Specialities, July 1967, pages 70–78 and 162, continued in Soap and Chemical Specialities, Aug. 1967, pages 70–74, 104 and 106, and in J.Soc. Cosmetic Chemists 20, (August 1969) 577–593, Sanders describes a series of studies on aerosol emulsion systems based on certain polyoxyethylene fatty ethers in combination with certain long chain fatty acids and alcohols. Again, increases in emulsion viscosity and stability and increases in foam stability and stiffness were noted. Whilst, since such systems are soap free, the problem of hard water scum does not arise, it has been found that such systems have a particular disadvantage in that they lack storage stability, particularly at moderately elevated temperatures, e.g. 30°–40°C, which in practice may well occur when the products are stored or placed on display, for example, in a shop window exposed to bright sunlight or are used in a hot climate. Under these conditions, compositions containing a synthetic surfactant solution and a long chain fatty alcohol or acid, as described in these articles, undergo an irreversible phase separation, that is to say they cannot be redispersed merely by hand shaking by the user, with the result that the emulsion no longer foams, or foams inadequately upon discharge from the container. Such products therefore lack the necessary shelf-life. In addition, separated solid phase material may block the valve and discharge apertures and thus further contribute to the malfunction of the container.

Other aerosol emulsions based on synthetic surfactants that have been tested suffer from other defects such as emulsion instability, noisy discharge from the container, inadequate foam formation and foam stability.

OBJECT OF INVENTION

A need therefore exists for an improved aerosol shaving foam preparation based on synthetic surfactants and which is therefore not liable to scum formation when used in hard water conditions, but which is storage stable, particularly at mildly elevated temperatures and is satisfactory in other respects, such as foam volume and density, foam stability, foam feel, and quiet operation.

STATEMENT OF INVENTION

According to the present invention we have discovered a novel combination of surfactants which gives rise to improved aerosol shaving foam systems, in particular, to aerosol emulsions of good shelf life at moderately elevated temperatures, and which are scum free, notwithstanding the presence, in the preferred compositions of a proportion of soap. Moreover, not only are the compositions non-scum forming, even in hard water conditions, but they are also scum dispersing. That is to say, they have the capacity to disperse scum formed, for example, by washing the face with soap prior to shaving. The use of the aerosol shaving foams according to the invention therefore greatly facilitates the subsequent cleaning of the wash basin after washing and shaving.

According to the present invention there is provided a shaving foam package comprising a pressurised dispenser equipped with a dispensing head and valve and containing therein an aerosol emulsion comprising an aqueous concentrate containing (i) from 1.5–15% by weight, based on the weight of the concentrate, of one or more water-soluble or substantially water-soluble synthetic anionic-compatible surfactants; (ii) from 0.5 to 6.0% by weight, based on the weight of the concentrate, of one or more water-insoluble long chain fatty alcohols, and (iii) from 2–12% by weight, based on the weight of the concentrate, of an anionic surfactant selected from alkali metal or alkanolamine soaps, i.e. salts of fatty acids containing from 10–22 carbon atoms, long chain alkyl and alkaryl sulphates and ether sulphates, long chain alkyl and alkaryl sulphonates, long chain N-acyl sarcosinates, and mixtures of two or more thereof, the anionic surfactant constituting component (iii) being of a different type from that constituting component (i) when the latter is itself anionic; and emulsified therewith a normally gaseous propellant in liquid phase; the weight ratio of total surfactant, i.e. components (i) and (iii) together, to long chain fatty alcohol being from 1:1 to 20:1 and the weight ratio of total synthetic surfactant plus long chain fatty alcohol, to soap, when said anionic surfactant is or contains soap, being in the range 0.5:1 to 4:1.

DETAILED DESCRIPTION

The first component of the aqueous concentrates used in the present invention is a water soluble or substantially water soluble synthetic, anionic-compatible surfactant. By substantially water soluble, we mean a surfactant which is self-dispersible in water, and by anionic-compatible we mean capable of existing in admixture in aqueous solution with anionic surfactants of the type specified under (iii) without precipitation or loss of surface active properties. Thus, component (i) may be nonionic, anionic, amphoteric or weakly cationic in character, although nonionic surfactants are preferred. The nonionic surfactants which are useful in the present invention are alkylene oxide (i.e. ethylene or propylene oxide) adducts of long chain fatty alcohols, acids or amides, of polyol esters of long chain fatty acids, and of long chain alkyl phenols, polyoxyethylene adducts of polyoxypropylene glycols, the latter adducts being commercially available under the trade mark 'Pluronic', long chain fatty acid alkanolamides, and polyol (e.g. sucrose) esters of long chain fatty acids. Suitable anionic surfactants are long chain alkyl and alkaryl esters of phosphorus acids, long chain alkyl and alkaryl sulphosuccinates, N-acyl-N-alkyl taurates and beta sulphoethers of long chain fatty acids. Component (i) may also be a long chain alkyl or alkaryl sulphate or ether sulphate, a long chain alkyl or alkaryl sulphonate or a long chain N-acyl sarcosinate, provided that component (iii) is then either a soap or a different synthetic anionic surfactant from this selected group. By 'different' in this context we mean of 'different type' e.g. an ether sulphate or a sulphonate as opposed to a sulphate or vice versa, or a sarcosinate as opposed to a sulphate or sulphonate or vice versa, and not anionic surfactants differing only with respect to the cation, e.g. a sodium as opposed to a potassium alkyl sulphate, or only with respect to the size of the alkyl or alkaryl group, e.g. an octyl ether sulphate as opposed to a nonyl ether sulphate. Suitable amphoteric surfactants are long chain alkyl amino acids, betaines, sulphobetaines and imidazolines. Other suitable surfactants are ethylene oxide and propylene oxide adducts of long chain fatty amines and long chain alkyl and alkaryl amine oxides.

Within the above definitions and throughout this specification and claims the expression 'long chain' when used in expressions such as 'long chain fatty acid', 'long chain fatty alcohol', 'long chain alkyl' is intended to cover groups containing from 12–18 carbon atoms, whilst the expression 'long chain alkaryl' is intended to cover alkyl-substituted aryl groups comprising a benzene or naphthalene nucleus substituted by a $C_5$–$C_{12}$ alkyl substituent.

As already indicated, the preferred synthetic surfactants are the nonionics, particularly the polyoxyethylene adducts of long chain fatty alcohols, acids and amides containing from 8–60 ethylene oxide units. Especially preferred are polyoxyethylene adducts of $C_{12}$–$C_{18}$ alcohols containing from 10–30 ethylene oxide units.

Other synthetic surfactants of interest are nonyl phenoxypolyoxyethylene (50) ethanol, polyoxyethylene (20) sorbitan monostearate, the sodium salt of the 2-sulphoethyl ester of coconut oil acid, and polyoxyethylene adducts of stearylamine.

The second component of the aqueous concentrate used in this invention is a long chain fatty alcohol, i.e. containing 12–18 carbon atoms. Particularly preferred is tetradecyl alcohol (myristyl alcohol).

The third component of the aqueous concentrate is the anionic surfactant. Of these the soaps, i.e. the alkali metal and alkanolamine salts, particularly the sodium and potassium and the diethanolamine and triethanolamine salts, of long chain fatty acids, e.g. lauric acid, myristic, palmitic and stearic acid, are preferred, and it is a particularly surprising discovery of this invention that these soaps are effective, when present in small amount, to stabilize the synthetic surfactant/propellant emulsion and to enable ready redispersion of the emulsion by hand shaking of the package even after standing for long periods of time and at moderately elevated temperature. The other anionic surfactants which serve the same purpose are long chain alkyl and alkaryl sulphates and ether sulphates, long chain alkyl and alkaryl sulphonates and long chain N-acyl sarcosinates. Mixtures of two or more may be used as well as mixtures thereof with soap. Also, as already indicated, such anionic surfactants may be present as component (*i*) in those cases where component (*iii*) is a soap, or where component (*iii*) is a different one of this selected group.

When using an anionic material other than soap, preferred materials are lauryl sulphates, lauryl ether sulphates, octyl phenyl sulphonates, nonyl phenyl sulphonates, and sodium lauroyl sarcosinate.

In the aqueous concentrates used in the present invention the amount of synthetic surfactant (component (*i*)) will be in the range 1.5–15% by weight based on the weight of the concentrate, with 4–10% by weight preferred, and the amount of long chain alcohol will be from 0.5 to 6.0% by weight, preferably 1–3% and in order to provide a satisfactory balance of properties the weight ratio of total surfactant (i.e. components (*i*) and (*iii*) together) to long chain fatty alcohol will be from 1:1 to 20:1, preferably 3:1 to 10:1.

The anionic surfactant (component (*iii*)) will generally be present in an amount of from 2–12% by weight based on the weight of the concentrate, with the preferred amounts depending on whether a soap or synthetic anionic surfactant is used. In the former case the amount of soap is preferably from 2–7% by weight, and more preferably 3–6% by weight. These figures may be contrasted with the amount of soap normally present in commercially available aerosol shaving foam preparations based on aqueous soap solutions which normally contain from 10–15% by weight of soap based on the weight of the concentrate. Where a synthetic anionic surfactant as component (*iii*) is used in the compositions of this invention, the amount is preferably in the range 3–6% by weight but can be as high as 12%.

Where a synthetic anionic surfactant is used as component (*iii*) the amount relative to the synthetic surfactant of component (*i*) is not critical, but where soap is used, a balance must be maintained between the synthetic surfactant and soap in order to obtain emulsion stability on the one hand and scum free and scum dispersant properties on the other. Generally speaking, therefore, the weight ratio of total synthetic surfactant plus fatty alcohol to soap in the compositions of this invention should be in the range 0.5:1 to 4:1.

Generally speaking the total solids concentration of the aqueous concentrates used in the present invention will be from 5–30% by weight, preferably 8–20% by weight, based on the weight of the concentrate, but these amounts are not critical.

The propellants used in the compositions used in the present invention are conventional materials e.g. hydrocarbon and hydrocarbon mixtures, e.g. the mixture of butane, isobutane and propane known commercially as Butane 40, and halohydrocarbons such as dichlorodifluoromethane (12) on its own or mixtures thereof with dichlorotetrafluoroethane (114). Mixtures of hydrocarbon and halohydrocarbon propellants may also be used. The quantity of propellant used will generally be in the range 3–12% by weight of the total emulsion, depending on the propellant used, although the exact amount is by no means critical to this invention. Generally speaking, hydrocarbon propellants such as butane mixtures will be used in amounts at the lower end of the stated range, e.g. 3–7%, whilst halohydrocarbon propellants will be used in amounts at the upper end of the range, e.g. 7–12%. Generally preferred as propellants will be the halohydrocarbons, particularly fluorocarbons, and mixtures thereof with hydrocarbons. Hydrocarbon propellants on their own are less preferred.

Other ingredients such as antioxidants, perfuming agents, stabilizers, viscosity modifiers, humectants, emollients and lubricants, may be included in the compositions of this invention as is conventional in the art.

Examples of aerosol shaving foam preparations according to the invention are as follows. Each composition was packaged in a conventional pressurised dispenser equipped with conventional discharge valve and foam dispensing head.

Example 1

|  | % W/W |
|---|---|
| Polyoxyethylene(4)lauryl ether | 1.66 |
| Myristyl alcohol | 2.02 |
| Triethanolamine myristate | 1.83 |
| Triethanolamine palmitate | 2.75 |
| Water | 83.34 |
| Propellant: 12/114 (40:60) | 8.40 |

Example 2

| | |
|---|---|
| Polyoxyethylene(23)lauryl ether | 5.50 |
| Myristyl alcohol | 2.02 |
| Potassium myristate | 5.50 |
| Isopropanol | 3.66 |
| Water | 74.92 |
| Propellant: 12/114 (40:60) | 8.40 |

Example 3

| | |
|---|---|
| Polyoxyethylene(10) cetyl ether | 2.75 |
| Myristyl alcohol | 1.83 |
| Triethanolamine laurate | 2.15 |
| Triethanolamine stearate | 4.40 |
| Isopropanol | 1.83 |
| Glycerol | 5.00 |
| Water | 73.64 |
| Propellant: 12/114 (40:60) | 8.40 |

Example 4

| | |
|---|---|
| Polyoxyethylene(20)stearyl ether | 5.42 |
| Myristyl alcohol | 2.07 |
| Potassium laurate | 0.94 |
| Triethanolamine palmitate | 2.83 |
| Water | 82.93 |
| Propellant: 12/114 (40:60) | 4.24 |
| butane 40 | 1.57 |

Example 5

| | |
|---|---|
| Hydrogenated tallow amide ethoxylated with 50 moles ethylene oxide (Ethomide HT60) | 11.77 |
| Myristyl alcohol | 2.07 |
| Triethanolamine laurate | 0.94 |
| Triethanolamine palmitate | 2.83 |
| Isopropanol | 2.83 |
| Water | 73.75 |
| Propellant: 12/114 (40:60) | 4.24 |
| butane 40 | 1.57 |

Example 6

| | |
|---|---|
| Poly(ethyleneglycol)1000 monostearate (Cithrol 10MS) | 6.12 |
| Myristyl alcohol | 2.07 |
| Triethanolamine laurate | 0.94 |
| Triethanolamine palmitate | 2.83 |
| Isopropanol | 2.83 |
| Water | 79.40 |
| Propellant: 12/114 (40:60) | 4.24 |
| butane 40 | 1.57 |

Example 7

| | |
|---|---|
| Nonylphenoxypolyoxyethylene (50) ethanol (Antarox CO 970) | 11.30 |
| Myristyl alcohol | 2.07 |
| Triethanolamine laurate | 0.94 |

-continued

| | |
|---|---|
| Triethanolamine palmitate | 2.83 |
| Isopropanol | 2.83 |
| Water | 74.22 |
| Propellant: 12/114 (40:60) | 4.24 |
| butane 40 | 1.57 |

Example 8

| | |
|---|---|
| Polyoxyethylene (20) sorbitan monostearate (Tween 60) | 5.92 |
| Myristyl alcohol | 2.13 |
| Triethanolamine myristate | 1.93 |
| Triethanolamine palmitate | 2.90 |
| Water | 83.82 |
| Propellant: butane 40 | 3.30 |

Example 9

| | |
|---|---|
| Tallow monoethanolamide ethoxylate (Empilan LN8) | 4.58 |
| Myristyl alcohol | 1.83 |
| Triethanolamine myristate | 2.75 |
| Triethanolamine palmitate | 2.75 |
| Glycerol | 5.00 |
| Water | 74.69 |
| Propellant: 12/114 (40:60) | 8.40 |

Example 10

| | |
|---|---|
| ABA Block copolymer of propylene oxide and ethylene oxide. MWt = 7700. (Pluronic F87) | 2.75 |
| Myristyl alcohol | 1.83 |
| Triethanolamine myristate | 1.83 |
| Triethanolamine palmitate | 2.75 |
| Water | 82.44 |
| Propellant: 12/114 (40:60) | 8.40 |

Example 11

| | |
|---|---|
| Sodium lauroyl sarcosinate | 4.58 |
| Myristyl alcohol | 3.21 |
| Triethanolamine myristate | 1.83 |
| Triethanolamine palmitate | 2.75 |
| Isopropanol | 2.75 |
| Water | 76.48 |
| Propellant: 12/114 (40:60) | 8.40 |

Example 12

| | |
|---|---|
| Coconut acid ester of sodium isethionate (83% active). (Fenopon AC78) | 4.58 |
| Myristyl alcohol | 0.92 |
| Triethanolamine myristate | 1.81 |
| Triethanolamine palmitate | 1.81 |
| Water | 82.48 |
| Propellant: 12/114 (40:60) | 8.40 |

Example 13

| | |
|---|---|
| Fenopon AC78 | 4.58 |
| Myristyl Alcohol | 2.75 |
| Sodium lauroyl sarcosinate | 4.58 |
| Water | 79.69 |
| Propellant: 12/114 (40:60) | 8.40 |

Example 14

| | |
|---|---|
| Ammonium salt of sulphated nonylphenoxy-poly(ethyleneoxy) ethanol (60% active). (Fenopon CO436) | 7.34 |
| Myristyl alcohol | 5.37 |
| Triethanolamine myristate | 1.83 |
| Triethanolamine palmitate | 2.75 |
| Water | 74.31 |
| Propellant: 12/114 (60:40) | 8.40 |

Example 15

| | |
|---|---|
| Sulphonated Amide. (Pyrotex 271 DF) | 2.75 |
| Myristyl alcohol | 1.83 |
| Triethanolamine myristate | 0.92 |
| Triethanolamine palmitate | 0.92 |
| Water | 85.18 |
| Propellant: 12/114 (40:60) | 8.40 |

Example 16

| | |
|---|---|
| Sodium sulphosuccinate of lauryl alcohol polyglycol ether (40% active). (Condanol SB FA/1) | 5.73 |
| Myristyl alcohol | 2.02 |
| Triethanolamine myristate | 0.61 |
| Triethanolamine palmitate | 3.66 |
| Water | 79.58 |
| Propellant: 12/114 (40:60) | 8.40 |

Example 17

| | |
|---|---|
| Coconut imidazoline derivative (50% active) (Crodateric C) | 3.30 |
| Myristyl alcohol | 1.92 |
| Triethanolamine myristate | 3.66 |
| Water | 82.72 |
| Propellant: 12/114 (40:60) | 8.40 |

Example 18

| | |
|---|---|
| Coconut amino sulphonate (50% active). (Varion 1017) | 2.75 |
| Myristyl alcohol | 1.83 |
| Triethanolamine myristate | 1.83 |
| Triethanolamine palmitate | 2.75 |
| Water | 82.44 |
| Propellant: 12/114 (40:60) | 8.40 |

-continued

Example 19

| | |
|---|---|
| Fatty amine derivative with betaine structure. (30% active). (Dehyton AB 30) | 9.15 |
| Myristyl alcohol | 1.83 |
| Triethanolamine myristate | 1.83 |
| Triethanolamine palmitate | 2.75 |
| Water | 76.04 |
| Propellant: 12/114 (40:60) | 8.40 |

Example 20

| | |
|---|---|
| Stearylamine ethoxylated with 50 moles of ethylene oxide. (Ethomeen 18/60) | 3.78 |
| Sodium lauryl ether sulphate | 4.73 |
| Myristyl alcohol | 4.35 |
| Triethanolamine laurate | 0.95 |
| Triethanolamine palmitate | 2.36 |
| Isopropanol | 3.78 |
| Sorbitol | 1.35 |
| Fragrance | 0.30 |
| Water | 72.59 |
| Propellant: 12/114 (40:60) | 4.24 |
| butane 40 | 1.57 |

Example 21

| | |
|---|---|
| Sodium lauryl ether sulphate | 6.50 |
| Lauric diethanolamide | 0.70 |
| Myristyl alcohol | 2.77 |
| Cetyl alcohol | 0.10 |
| Triethanolamine laurate | 0.75 |
| Triethanolamine palmitate | 2.63 |
| Glycerol | 4.20 |
| Fragrance | 0.30 |
| Water | 72.15 |
| Propellant: 12/114 (60:40) | 8.30 |

Example 22

| | |
|---|---|
| Lauric diethanolamide | 4.80 |
| Polyoxyethylene (20) cetyl ether | 4.80 |
| Myristyl Alcohol | 1.92 |
| Triethanolamine myristate | 0.94 |
| Triethanolamine palmitate | 2.83 |
| Propylene glycol | 0.75 |
| Glycerol | 3.25 |
| Fragrance | 0.30 |
| Water | 72.11 |
| Propellant: 12/114 (60:40) | 8.30 |

To illustrate the storage stability of compositions according to this invention a series of aerosol shaving foam formulations were packaged in a transparent glass aerosol container and stored at elevated temperature for varying periods of time. At the end of that time the emulsion was inspected visually and tested for ease of redispersion and subsequent foaming. The results are described below in the following Experiments.

Experiment 1

As a control an aqueous concentrate was formulated containing

| | |
|---|---|
| Polyoxyethylene (20) cetyl ether | 5% by weight |
| Myristyl alcohol | 2% by weight |
| Glycerol | 5% by weight |
| Water | q.s.100% by weight |

The concentrate was packaged in a glass container and pressurised with a 60:40 weight ratio mixture of propellants 12 and 114. The total aerosol emulsion formed contained 91.6% by weight of concentrate and 8.4% by weight of propellant.

Upon shaking and subsequent operation of the valve, a rather wet unstable foam is discharged rather noisily.

After initial testing for foam formation, the package was stored for one month at temperatures in the range 40°–45°C. At the end of this time, the package was cooled to room temperature and re-examined. A solid white phase was apparent in the bottom of the container and this proved impossible to redisperse even on vigorous shaking by hand for 30 seconds.

Experiment 2

Experiment 1 was repeated but with the addition to the concentrate of 5% by weight of triethanolamine laurate.

On actuation of the valve a soft creamy foam is discharged with a smooth quiet flow.

Upon storage for 5 months at 40°–45°C a white heavy phase settled out, but this was readily redispersed when the container, cooled to room temperature, was shaken gently by hand five times. After storage the contents of the package still discharge smoothly as a soft creamy foam.

Experiment 3

Experiment 2 is repeated but using 5% sodium lauryl sulphate instead of triethanolamine laurate.

Immediately after packaging, the foam obtained on discharge is a thick creamy and stable foam.

No phase separation occurred after storage at 40–45°C for 5 months and no adverse effect on the foam forming properties was noted.

Experiment 4

Experiment 2 is repeated but using 5% of a sodium alkaryl sulphonate (DuPont:Alkanol DW) instead of triethanolamine laurate.

Immediately after packaging a soft slightly open foam is obtainable with smooth quiet expulsion.

Storage at 40°–45°C for 4 months caused phase separation, but on cooling to room temperature, the contents were readily redispersed by inversion of the container. After storage, the contents were discharged smoothly as a soft foam.

Experiment 5

Experiment 2 was repeated but using 5% sodium laurayl sarcosinate in place of triethanolamine laurate.

Initial foam assessment showed a good smooth expulsion and a soft creamy foam. Similar results were obtained after storage at 40°–45°C for five months followed by cooling to room temperature and gentle shaking to effect redispersions of separated materials.

Experiment 6

Essentially similar results are obtained as in Experiment 5, but with a somewhat thicker foam, using 5% triethanolamine lauryl ether sulphate in place of the sodium lauroyl sarcosinate.

The advantageously low scum formation properties and high scum dispersion properties of the compositions of this invention are illustrated by the following experiments.

Experiment 7

A series of 'standard' hard water solutions pH 7, were prepared having calcium ion concentrations equivalent to 45 ppm, 100 ppm and 180 ppm calcium carbonate.

An aerosol foam dispensed from a conventional soap based aerosol shaving foam dispenser containing approximately 15% by weight of soap, based on the weight of the aqueous concentrate, was stirred into each standard hard water solution at 45°C in an amount of approximately 1 gram per liter and each solution visually inspected for scum formation. At 45 ppm equivalent of calcium carbonate a light scum was visible, at 100 ppm a medium scum and at 180 ppm a heavy scum.

By way of comparison, the shaving foam obtained from the composition of Example 5 gave no deposit when stirred into a 'standard' hard water solution containing 4500 ppm equivalent of calcium carbonate under the same conditions, namely 45°C, pH 7 and in an amount of approximately 1 gram per liter.

The conventional soap-based foam when dispersed into distilled water showed a thin deposit believed to be free fatty acid. No such deposit was visible when the foam of Example 5 is dispersed in distilled water.

Experiment 8

A hard water scum was formed by adding 1 gram per liter of potassium palmitate to water at 45°C and pH 7, containing 400 ppm equivalent of calcium carbonate. Aqueous concentrates of the types used in this invention were added incrementally and the amount of concentrate required to disperse the scum was measured.

The scum was considered to be dispersed when the discrete particles of scum were no longer visible thereby leaving a pearlescent solution.

| Concentrate 1 | Wt.% |
| --- | --- |
| Tween 60 | 6.12 |
| Myristyl Alcohol | 2.20 |
| Triethanolamine myristate | 2.00 |
| Triethanolamine palmitate | 3.00 |
| Water | 86.68 |

| Concentrate 2 | Wt.% |
| --- | --- |
| Polyoxyethylene (20) cetyl ether | 5.00 |
| Myristyl Alcohol | 2.00 |
| Sodium lauryl sulphate | 4.00 |
| Glycerol | 5.00 |
| Water | 84.00 |

The minimum quantity of Concentrate 1 required to disperse the scum was 1.6 gram per liter of the hard water solution, equivalent to approximately 25c.c. of foam, and of Concentrate 2, 0.6 grams per liter, equivalent to approximately 9c.c. of foam. Essentially similar scum dispersion results are obtained when using a foam derived from these concentrates in place of the concentrate itself.

The conventional soap-based aerosol shaving foam when used in this test showed no scum dispersing activity but rather increased the amount of scum present.

We claim:

1. A shaving foam package comprising a pressurized dispenser equipped with a dispensing head and valve and containing therein a foam-forming composition consisting essentially of (A) an aqueous concentrate containing (i) from 1.5–15% by weight, based on the weight of the concentrate, of one or more water soluble or substantially water soluble synthetic anionic-compatible surfactants; (ii) from 0.5 to 6.0% by weight, based on the weight of the concentrate, of one or more water insoluble long chain fatty alcohols; and (iii) from 2–12% by weight, based on the weight of the concentrate, of an anionic surfactant selected from alkali metal or alkanolamine soaps, i.e. salts of fatty acids containing from 10–22 carbon atoms, long chain alkyl and alkaryl sulphates and ether sulphates, long chain alkyl and alkaryl sulphonates, long chain N-acyl sarcosinates, and mixtures of two or more thereof the anionic surfactant constituting (iii) being of a different type from that constituting component (i) when the latter is itself anionic, the balance of the concentrate being water; and emulsified therewith (B) a normally gaseous propellant in liquid phase; the weight ratio of total surfactant, i.e. components (*i*) and (*iii*) together, to long chain fatty alcohol being from 1:1 to 20:1 and the weight ratio of total synthetic surfactant plus long chain fatty alcohol, to soap, when said anionic surfactant is or contains soap, being in the range 0.5:1 to 4:1.

2. A package according to claim 1, wherein component (*i*) is a nonionic surfactant selected from ethylene oxide or propylene oxide adducts of long chain fatty alcohols, acids, and amides, ethylene oxide or propylene oxide adducts of polyol esters of long chain fatty acids, ethylene oxide or propylene oxide adducts of long chain alkyl phenols, polyoxyethylene adducts of polyoxypropylene glycol, long chain fatty acid alkanolamides and polyol esters of long chain fatty acids.

3. A shaving foam package comprising a pressurised dispenser equipped with a dispensing head and valve and containing therein a foam-forming emulsion consisting essentially of (A) an aqueous concentrate containing (*i*) from 1.5–15% by weight, based on the weight of the concentrate, of at least one water soluble or substantially water soluble synthetic nonionic surfactant; (*ii*) from 0.5–6.0% by weight, based on the weight of the concentrate, of myristyl alcohol; and (*iii*) from 2–7% by weight of a surfactant selected from alkali metal soaps and alkanolamine soaps and mixtures thereof, the balance of the concentrate being water; and emulsified therewith (B) a normally gaseous aerosol propellant in liquid phase; the weight ratio of components (*i*) and (*iii*) together to component (*ii*) being from 1:1 to 20:1; and the weight ratio of component (*i*) plus component (*ii*) to component (*iii*) being in the range of 0.5:1 to 4:1.

4. A package according to claim 3, wherein component (*i*) is a nonionic surfactant selected from ethylene oxide or propylene oxide adducts of long chain fatty alcohols, acids, and amides, ethylene oxide or propylene oxide adducts of polyol esters of long chain fatty acids, ethylene oxide or propylene oxide adducts of long chain alkyl phenols, polyoxyethylene adducts of polyoxypropylene glycol, long chain fatty acid alkanolamides and polyol esters of long chain fatty acids.

5. A shaving foam package comprising a pressurised dispenser equipped with a dispensing head and valve and containing therein a foam-forming emulsion consisting essentially of (A) an aqueous concentrate containing (*i*) from 1.5–15% by weight, based on the weight of the concentrate, of at least one water soluble or substantially water soluble synthetic nonionic surfactant; (*ii*) from 0.5–6.0% by weight, based on the weight of the concentrate, of myristyl alcohol; and (*iii*) from 3–6% by weight, based on the weight of the concentrate, of an anionic surfactant selected from long chain alkyl and alkaryl sulphates and ether sulphates, long chain alkyl and alkaryl sulphonates and long chain N-acyl sarcosinates, the balance of the concentrate being water; and emulsified therewith (B) a normally gaseous aerosol propellant in liquid phase; the weight ratio of components (*i*) and (*iii*) together to component (*ii*) being from 1:1 to 20:1.

6. A package according to claim 5, wherein component (*i*) is a nonionic surfactant selected from ethylene oxide or propylene oxide adducts of long chain fatty alcohols, acids, and amides, ethylene oxide or propylene oxide adducts of polyol esters of long chain fatty acids, ethylene oxide or propylene oxide adducts of long chain alkyl phenols, polyoxyethylene adducts of polyoxypropylene glycol, long chain fatty acid alkanolamides and polyol esters of long chain fatty acids.

7. A shaving foam package comprising a pressurised dispenser equipped with a dispensing head and valve and containing therein a foam-forming emulsion consisting essentially of (A) an aqueous concentrate containing (*i*) from 1.5–15% by weight, based on the weight of the concentrate, of a water soluble or substantially water soluble synthetic anionic surfactant selected from long chain alkyl and alkaryl sulphates and ether sulphates, long chain alkyl and alkaryl sulphonates, long chain N-acyl sarcosinates, and mixtures of two or more thereof; (*ii*) from 0.5–6.0% by weight, based on the weight of the concentrate, of myristyl alcohol; and (*iii*) from 2–7% by weight based on the weight of the concentrate of a surfactant selected from alkali metal soaps and alkanolamine soaps and mixtures thereof, the balance of the concentrate being water; and emulsified therewith (B) a normally gaseous aerosol propellant in liquid phase; the weight ratio of components (*i*) and (*iii*) together to component (*ii*) being from 1:1 to 20:1, and the weight ratio of component (*i*) plus component (*ii*) to component (*iii*) being from 0.5:1 to 4:1.

* * * * *

UNITED STATES PATENT OFFICE
CERTIFICATE OF CORRECTION

PATENT NO. : 3,959,160
DATED : May 25, 1976
INVENTOR(S) : CHRISTOPHER HORSLER ET AL

It is certified that error appears in the above-identified patent and that said Letters Patent are hereby corrected as shown below:

In the heading, after the line numbered "[21]" insert:

--[30] Foreign Application Priority Data

May 16, 1973  Great Britain........73 23410--

Column 8, line 54, after "glass" insert --aerosol--.

Column 9, line 38, correct the spelling of "lauroyl".

Signed and Sealed this

Tenth Day of August 1976

[SEAL]

Attest:

RUTH C. MASON
Attesting Officer

C. MARSHALL DANN
Commissioner of Patents and Trademarks